United States Patent
Ahoubim

(10) Patent No.: US 10,631,585 B2
(45) Date of Patent: Apr. 28, 2020

(54) PLEATED SPRAY TAN MASK AND METHOD OF DONNING

(71) Applicant: Tanaz Ahoubim, Encino, CA (US)

(72) Inventor: Tanaz Ahoubim, Encino, CA (US)

( * ) Notice: Subject to any disclaimer, the term of this patent is extended or adjusted under 35 U.S.C. 154(b) by 364 days.

(21) Appl. No.: 15/489,064

(22) Filed: Apr. 17, 2017

(65) Prior Publication Data

US 2018/0295907 A1    Oct. 18, 2018

(51) Int. Cl.
| | |
|---|---|
| A41D 13/11 | (2006.01) |
| A61F 9/04 | (2006.01) |
| A62B 23/02 | (2006.01) |
| A62B 18/08 | (2006.01) |

(52) U.S. Cl.
CPC .......... *A41D 13/1115* (2013.01); *A41D 13/11* (2013.01); *A41D 13/1184* (2013.01); *A61F 9/04* (2013.01); *A62B 18/082* (2013.01); *A62B 23/025* (2013.01)

(58) Field of Classification Search
CPC . A41D 13/11; A41D 13/1115; A41D 13/1161; A41D 13/1184; A62B 18/082; A62B 18/084; A62B 23/025; A61F 9/04; A61F 9/045
USPC ........ 128/858, 863; 2/10, 15, 417–419, 422, 2/424
See application file for complete search history.

(56) References Cited

U.S. PATENT DOCUMENTS

| | | | | | |
|---|---|---|---|---|---|
| 3,561,011 | A | * | 2/1971 | Gregg | A42B 1/045 2/204 |
| 4,825,878 | A | * | 5/1989 | Kuntz | A41D 13/11 128/207.11 |
| 4,969,473 | A | * | 11/1990 | Bothwell | A41D 13/11 128/858 |
| 5,561,863 | A | * | 10/1996 | Carlson, II | A41D 13/1115 128/206.19 |
| 6,055,982 | A | * | 5/2000 | Brunson | A41D 13/1115 128/205.27 |
| 6,532,598 | B1 | * | 3/2003 | Cardarelli | A41D 13/11 128/206.19 |
| 2005/0015838 | A1 | * | 1/2005 | Cheng | A41D 13/1184 2/9 |
| 2012/0199142 | A1 | * | 8/2012 | Nagao | A41D 13/1115 128/863 |
| 2014/0224261 | A1 | * | 8/2014 | Tsuei | A62B 23/025 128/863 |

\* cited by examiner

*Primary Examiner* — Keri J Nelson

(57) ABSTRACT

A pleated spray tan mask and method of donning is donned and attached around the face, so as to protect a user from inhaling undesired airborne particles or vapor while being spray tanned with tanning composition, and also to prevent tanning composition from coating the face. The mask comprises three panels that cover a portion of the face and perform independent functions for protecting against sprayed tanning compositions. The mask provides a forehead panel and a lower face panel that are pleated to increase in size for larger heads. Pleats allow the mask to be one-size-fits-all. Another unique feature of the forehead and lower face panels is that flaps form at the edges of the individual panels. Flaps fold inwardly and enhance airflow behind the panels. Further, a mid-face panel disposed between the forehead and lower face panels is at least partially transparent to enable visibility while being spray tanned.

19 Claims, 3 Drawing Sheets

PLEATED SPRAY TAN MASK AND METHOD OF DONNING

FIELD OF THE INVENTION

The present invention relates generally to a pleated spray tan mask and method of donning. More so, the present invention relates to a spray tan mask that is easily donned and attached around the face in a comfortable manner; whereby the spray tan mask comprises a forehead panel and a lower face panel that cover the forehead and the mouth, respectively and are fabricated from a filtering material that protects against the proportion of particles from a tanning composition, while allowing for breathability of the skin at the forehead and mouth region of the face; whereby the panel further comprises a transparent mid-face panel disposed between the forehead and lower face panels that allows for visibility to the user see while being spray tanned; whereby the forehead and lower face panels are pleated, so as to expand and thereby accommodate variously sized heads; whereby a plurality of cords attach from one end inside the edges of the panels, forming an outer flap at the edges of the panels that allow for air circulation and that also fold inwardly.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is recognized that spray-on, or sunless tanning is a cosmetic procedure that bronzes the skin to appear tanned by the sun. Spray tanning has a fast-acting nature and allows the user to avoid ultraviolet radiation while gaining the benefits of a tanned appearance on the skin, and often the face. However, the spray tanning process involves spraying a tanning composition that comprises particles, which can be dangerous to breath.

Typically, the spray tanning is a form of sunless tanning where a fine tanning composition mist is sprayed onto your body. This mist has an ingredient in it called Dihydroxyacetone (DHA) that interacts with the skin's chemistry to turn it tan, or bronze. This temporary effect generally lasts from 3-7 days and is completely safe for your skin, although spray tanning does not always provide any protection against the sun's rays.

The mist can be sprayed from a variety of spraying devices. First, a user generally goes to a tanning or beauty salon and have it applied in a booth. These specially-designed booths have several nozzles or jets that spray your entire body with the spray tanning solution. Second, a spray tan can be administered with an airbrush or air gun as they're called. Last, you can get a spray tan from a bottle.

The booth or technician then sprays your entire body with a fine mist. Once the composition is blended in, the tanning process is complete. This can be easier and less time-consuming than spreading a lotion or gel all over entire body. Another benefit of spray tanning is the fact that it dries quicker than many self-tanning products. Consequently, the tanning composition is less likely to get all over your clothes and the bed. As for the color achieved with spray tanning, that varies from person to person. Some people like the color and evenness you get with spray tanning, others think self-tanning lotions and gels are better.

Often, a mask or goggles are worn while the tanning composition is being sprayed on. The mask or googles protect the user from inhaling undesired airborne particles or vapor while at the same time maintaining both hands free. In many instances, the mask has a mouthpiece and a nose cover and can be held in position in the mouth and can even include a filter in the nose cover and may include a filter in the mouthpiece. However, the mask can be restrictive, and the goggles can only cover the mid-faces. The goggles also leave a circular mark around the perimeter of the mid-faces, which can be an undesirable look.

Furthermore, the mask can be restrictive and cumbersome. This can be problematic, since the user must hold their breath during the application and during the time required for the spray to clear. Further, if the spray tanning operation is performed in an open area, the coating should take about 5 to 15 seconds and the clearing of residues should take 1 to 10 seconds. Thus, the person would need to hold their breath for 6 to 25 seconds. Alternatively, the user could wear a filter over their mouth, have a filter inside of their mouth, or use a breathing tube.

Other proposals have involved spray tanning masks and goggles. The problem with these masking devices is that they do not allow the user to see through the mask clearly. Also, they do not expand to fit around larger heads or allow for comfortable breathing and talking while donning the mask. Even though the above cited masking devices meets some of the needs of the market, a pleated spray tan mask that is easily donned and attached around the face in a comfortable manner; and whereby the spray tan mask comprises a forehead panel and a lower face panel that cover the forehead and the mouth, respectively and are fabricated from a filtering material that protects against the proportion of particles from a tanning composition, while allowing for breathability of the skin at the forehead and mouth region of the face; and whereby the panel further comprises a transparent mid-face panel disposed between the forehead and lower face panels that allows for visibility to the user see while being spray tanned is still desired.

SUMMARY

Illustrative embodiments of the disclosure are generally directed to a pleated spray tan mask and method of donning. The pleated spray tan mask is easily donned and attached around the face in a comfortable manner, so as to protect a user from inhaling undesired airborne particles or vapor while being spray tanned with a spray tan composition, and also to prevent spray tan composition from coating the face. The pleated spray tan mask utilizes pleats along the individual panels to enable size expandability, and flaps at the edges to enhance airflow behind the mask, and also fold inwardly.

The spray tan mask comprises a forehead panel and a lower face panel that cover the forehead and the mouth, respectively and are fabricated from a filtering material that protects against the proportion of particles from a tanning composition. The panels are designed to allow for breathability of the skin at the forehead and mouth region of the face. The forehead panel is configured to substantially cover the four head. The forehead panel is defined by a pair of forehead longitudinal edges, a pair of forehead lateral edges, a forehead inner surface, and a forehead outer surface. The forehead panel is generally elongated, flat, and resilient. A plurality of upper pleats extend along the length of the forehead panel. The pleats enhance comfort along the forehead allow the forehead panel to expand, so as to fit larger heads.

Similarly, the lower face panel configured to substantially cover the mouth and cheek areas. The lower face panel is defined by a pair of lower face longitudinal edges, a pair of lower face lateral edges, a lower face inner surface, and a lower face outer surface. The lower face panel is generally elongated, flat, and resilient. A plurality of lower pleats extend along the length of the lower face panel. The lower pleats enhance comfort along the mouth, cheek, and jaws while speaking and also facilitate fitting around larger heads. Thus, the forehead and lower face panels are pleated, so as to expand and thereby accommodate variously sized heads.

In some embodiments, the mask further comprises a mid-face panel that is defined by a pair of mid-face longitudinal edges, a pair of mid-face lateral edges, a mid-face inner surface, and a mid-face outer surface. The mid-face panel is disposed between the forehead and lower face panels, and is configured to generally cover the eyes and middle area of the face. The mid-face panel allows for visibility. For example, the user can see through the mid-face panel while being spray tanned. The mid-face panel is generally elongated, resilient, and at least partially transparent. However, unlike the forehead panel and the lower face panel, the mid-face panel is not pleated, since pleats may compromise a clear vision.

In other embodiments, a plurality of cords attach from a predetermined distance away from the lateral edges of the forehead and lower face panels. By not attaching the cords at the lateral edges, a space is created that forms an outer flap at the lateral edges of the forehead and lower face panels.

In one aspect, the pleated spray tan mask comprises:
a forehead panel defined by a pair of forehead longitudinal edges, a pair of forehead lateral edges, and a forehead outer surface, the forehead panel being generally elongated, flat, and resilient;
a plurality of upper pleats forming on the forehead outer surface, the plurality of upper pleats extending along the length of the forehead panel, the plurality of upper pleats configured to enable expansion of the forehead panel;
a lower face panel defined by a pair of lower face longitudinal edges, a pair of lower face lateral edges, and a lower face outer surface, the lower face panel being generally elongated, flat, and resilient;
a plurality of lower pleats forming on the lower face outer surface, the plurality of lower pleats extending along the length of the lower face panel, the plurality of lower pleats configured to enable expansion of the lower face panel;
a mid-face panel defined by a pair of mid-face longitudinal edges, a pair of mid-face lateral edges, a mid-face inner surface, and a mid-face outer surface, the mid-face panel being at least partially transparent, the mid-face panel further being generally elongated, flat, and resilient;
a plurality of upper cords configured to enable fastening of the forehead panel and the mid-face panel, the plurality of upper cords defined by an upper mount end and an upper free end, the upper mount end disposed to fixedly attach to the pair of forehead lateral edges; and
a plurality of lower cords configured to enable fastening of the lower face panel and the mid-face panel, the plurality of lower cords defined by a lower mount end and a lower free end, the lower mount end disposed to fixedly attach at a lower predetermined distance from the pair of lower face lateral edges,
whereby a lower flap forms in the region of the lower predetermined distance.

In another aspect, the plurality of upper pleats extend between the pair of forehead lateral edges.

In another aspect, the plurality of lower pleats extend between the pair of lower face lateral edges.

In another aspect, the mid-face panel includes at least one of the following: a soft polyvinyl chloride, a Poly(methyl methacrylate), a polyethylene, and a silicone.

In another aspect, the plurality of upper cords comprises two strings.

In another aspect, the plurality of lower cords comprises four strings.

In another aspect, the lower predetermined distance between the lower mount end of the plurality of lower cords and the pair of lower face lateral edges is approximately between ¼ inch to 2 inches.

In another aspect, the plurality of upper and lower cords may include string fasteners, rubber bands, and elastic ropes.

In another aspect, the pair of forehead longitudinal edges and the pair of forehead lateral edges are reinforced.

In another aspect, the pair of lower face longitudinal edges and the pair of lower face lateral edges are reinforced.

In another aspect, the forehead panel comprises a filtering material.

In another aspect, the lower face panel comprises the filtering material.

In another aspect, the filtering material comprises a particulate filter.

One objective of the present invention is to provide a spray tan mask that inhibits contamination from spray tanning composition particulates.

Another objective is to provide a forehead panel and a lower face panel that are pleated to expand the panels.

Yet another objective is to provide a mid-face panel that is at least partially transparent, so that a user can see while being spray tan.

Yet another objective is to provide cords that attach inside the lateral edges of the panels, so that flap is created.

Yet another objective is to provide flaps that enhance airflow behind the panels and that also fold inwardly.

Yet another objective is to provide soft, flexible panel that are comfortable against the skin.

Yet another objective is to provide an inexpensive to manufacture pleated spray tan mask.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

Figure 1:
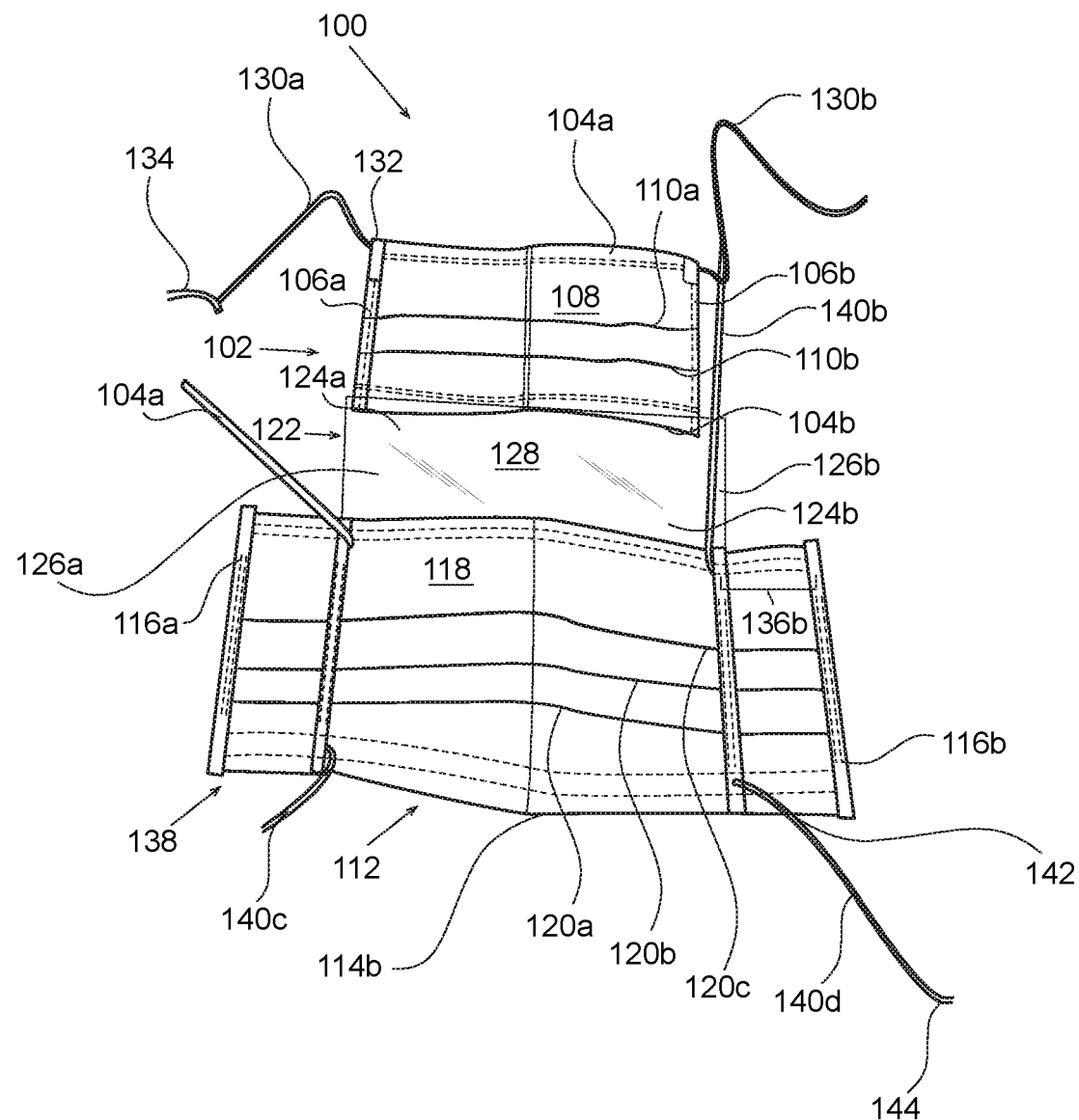
FIG. 1 illustrates a perspective view of an exemplary pleated spray tan mask, in accordance with an embodiment of the present invention.
Figure 2:
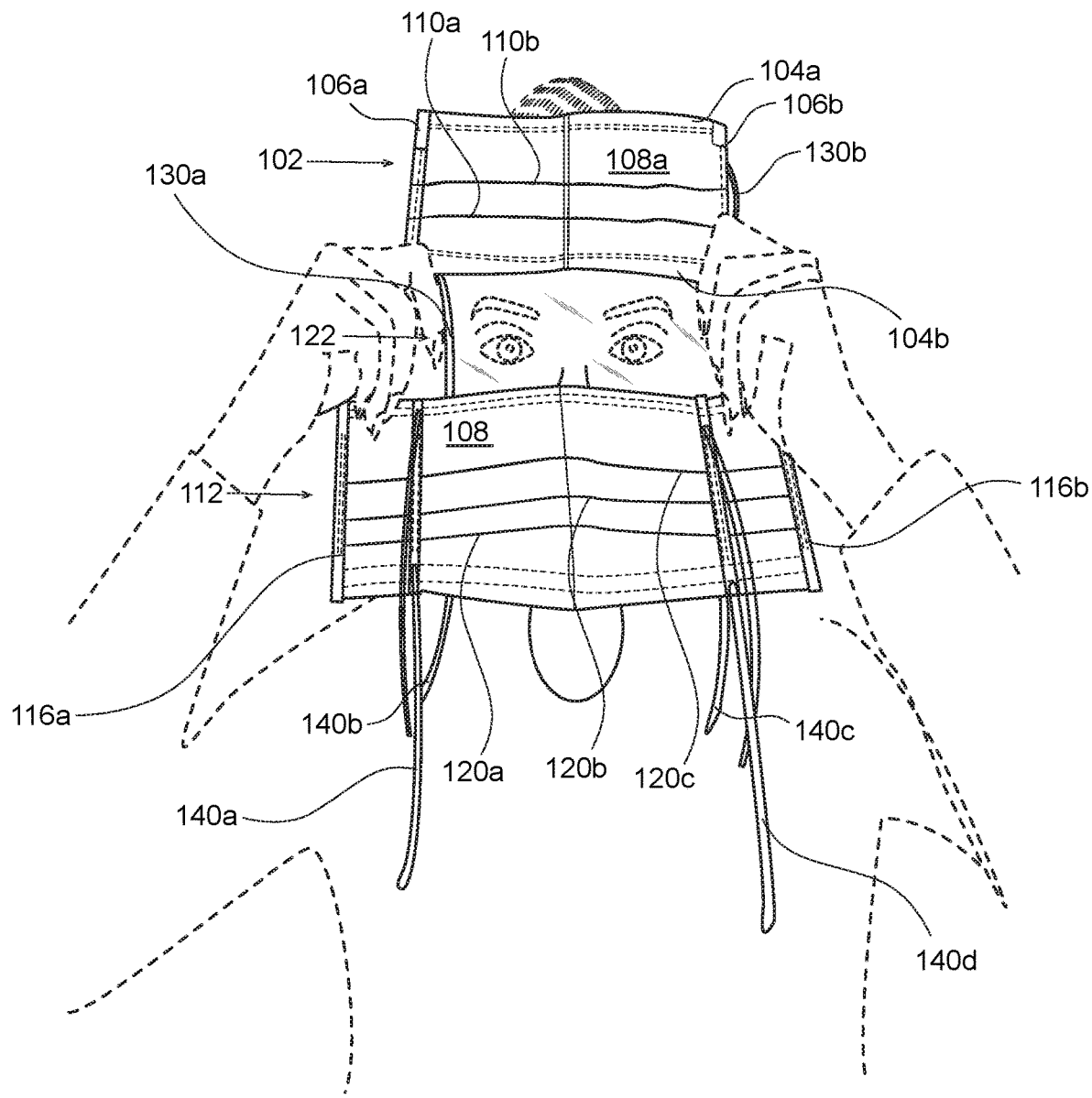
FIG. 2 illustrates a perspective view of the pleated spray tan mask shown in FIG. 1 being donned, in accordance with an embodiment of the present invention.
Figure 3:
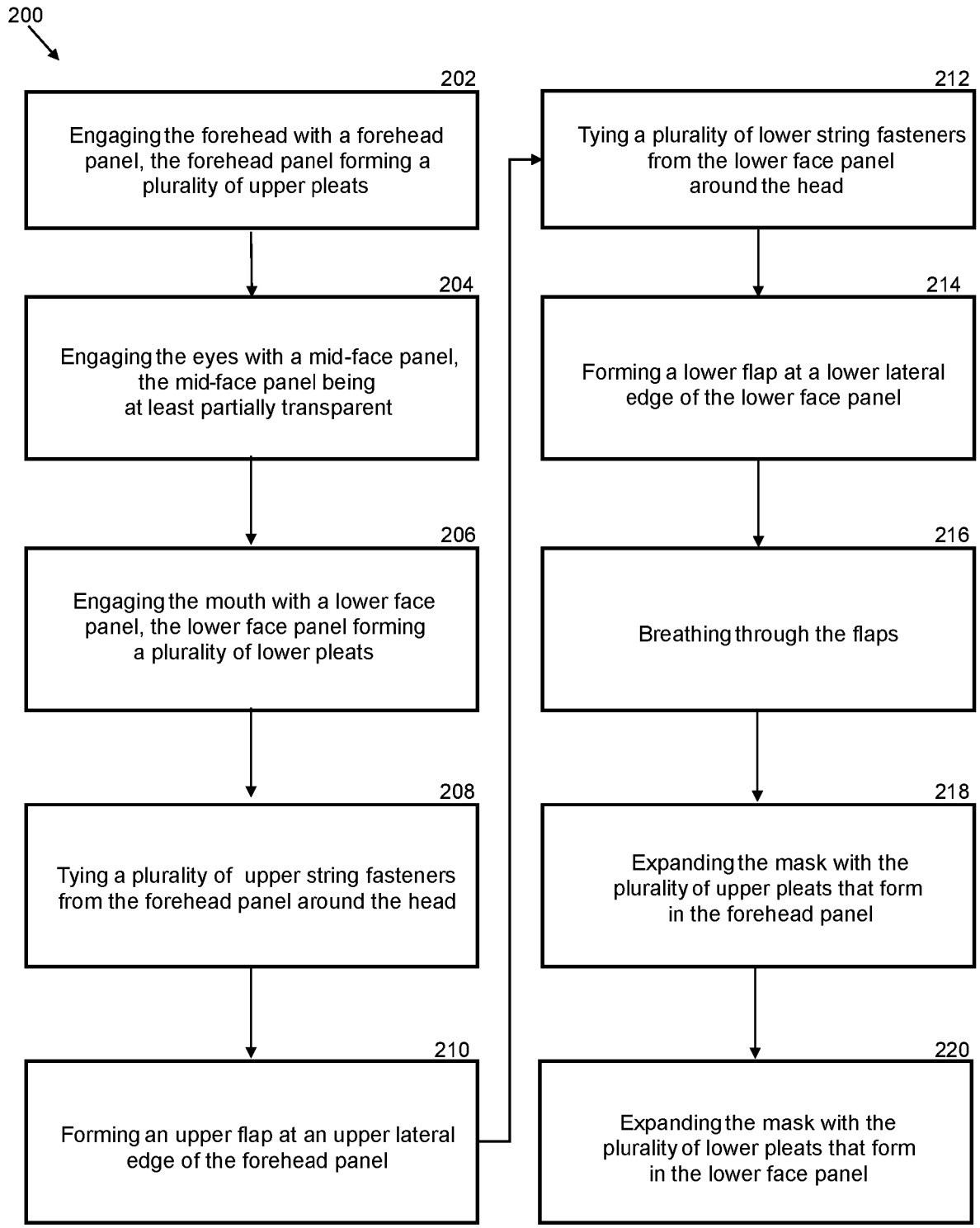
FIG. 3 illustrates a flowchart diagram of an exemplary method for donning a pleated spray tan mask, in accordance with an embodiment of the present invention.

A pleated spray tan mask 100 and method 200 of donning is referenced in FIGS. 1-3. The pleated spray tan mask 100 is easily donned and attached around the face in a comfortable manner, so as to protect a user from inhaling undesired airborne particles or vapor while being spray tanned with a spray tan composition, and also to prevent spray tan composition from coating the face. The pleated spray tan mask 100, hereafter "mask 100" provides three unique panels 102, 112, 122 that cover a portion of the face and perform independent functions that create a synergy for protecting the face and head areas against sprayed tanning compositions.

Looking initially at FIG. 1, the mask 100 is unique in that a forehead panel 102 and a lower face panel 112 cover their respective regions of the face, and are also pleated, so as to increase in size when the mask 100 is donned on larger heads. The pleats allows the mask 100 to be one-size-fits-all. Another unique feature of the forehead and lower face panels 102,112 is that a flap 138 formed at the edges of the lower face panel 112. Flap 138 folds inwardly and enhances airflow around the mouth and nose. Further, a mid-face panel 122, which is disposed between the forehead and lower face panels 102,112 is at least partially transparent to enable visibility for the user while being spray tanned.

Those skilled in the art will recognize that spray tanning is a form of sunless tanning where a fine tanning composition mist is sprayed onto your body. This mist has an ingredient in it called Dihydroxyacetone (DHA) that interacts with the skin's chemistry to turn it tan, or bronze. Unfortunately, the tanning composition used in the spray tanning process comprise particles that form a composition dangerous to breath.

The mask 100, and specifically the three panels 102, 112, 122 that form the mask 100, form an effective, ventilated barrier for a user to don while receiving a spray tan. The mask 100 protects against the proportion of particles that remaining airborne and do not coat the intended body sections of the skin. Thus, in many instances, the mask 100 is the last line of defense against airborne particles to protect the health of the user. Further, the mask 100 is configured to expand, so as to fit larger heads and provide a comfortable fit for all head sizes.

As referenced in FIG. 1, the spray tan mask 100 comprises a forehead panel 102 and a lower face panel 112 that cover the forehead and the mouth, respectively. The panels 102, 112 are fabricated from a filtering material that protects against the proportion of particles from a tanning composition. In one embodiment, the filtering material comprises a particulate filter. The forehead and lower face panels 102, 112 are designed to allow for breathability of the skin at the forehead and mouth region of the face. The transparent mid-face panel 122 is adjacently disposed, and coplanar between the forehead and lower face panels 102,112.

As illustrated in FIG. 2, the forehead panel 102 substantially covers the forehead, and an upper region of the face. The forehead panel 102 is generally elongated, flat, and resilient. The forehead panel 102 is defined by a pair of forehead longitudinal edges 104a, 104b, a pair of forehead lateral edges 106a, 106b, and a forehead outer surface 108. In some embodiments, the pair of forehead longitudinal edges 104a, 104b and the pair of forehead lateral edges 106a, 106b are reinforced. This can be useful when the forehead panel 102 is stretched across the forehead. In one embodiment, the forehead panel 102 is generally rectangular in shape. Though in other embodiments, the forehead panel 102 may have an oval or square shape.

In some embodiments, a plurality of upper pleats 110a, 110b form on the forehead outer surface 108. The upper pleats 110a, 110b extend along the length of the forehead panel 102. The pleats enhance comfort along the forehead by expanding when a larger head dons the mask 100. In one embodiment, the plurality of upper pleats 110a, 110b extend between the pair of forehead lateral edges 106a, 106b.

In other embodiments, a plurality of upper cords 130a, 130b attach to the upper lateral edges 106a-b of the forehead panel 102. The upper cords 130a, 130b may include two cords, strings, bands, and such that can be tied behind the head as the forehead panel 102 is oriented over the upper region of the face, i.e. forehead, temples.

The upper cords 130a-b are defined by an upper mount end 132 and an upper free end 134. The upper mount end 132 is disposed to fixedly attach to the pair of forehead lateral edges 106a, 106b. The free ends 134 of the upper cords 130a-b can be tied together to secure the mask 100 to the forehead. Though, the cords 130a-b do not necessarily have to be tied around the head for the mask 100 to remain attached to the forehead or face. The plurality of upper cords 130a-b may include, without limitation, string fasteners, rubber bands, and elastic ropes.

Similarly, the lower face panel 112 substantially covers the mouth and cheek areas of the face. The lower face panel 112 is defined by a pair of lower longitudinal edges 114a, 114b, a pair of lower lateral edges 116a, 116b, and a lower face outer surface 118. In some embodiments, the pair of lower longitudinal edges 114a, 114b and the pair of lower lateral edges 116a, 116b are reinforced. This can be useful when the lower face panel 112 is stretched across the lower regions of the face, and especially when the mouth moves to speak. The lower face panel 112 is generally elongated, flat, and resilient. In one embodiment, the lower face panel 112 is generally rectangular in shape. Though in other embodiments, the lower face panel 112 may have an oval or square shape.

A plurality of lower pleats 120*a*, 120*b*, 120*c* form on the lower face outer surface 118. The lower pleats 120*a*, 120*b*, 120*c* extend along the length of the lower face panel 112. The lower pleats 120*a*, 120*b*, 120*c* enhance comfort along the mouth, cheek, and jaws. Thus, the forehead and lower face panels 102,112 are pleated, so as to expand and thereby accommodate variously sized heads. The lower pleats 120*a*, 120*b*, 120*c* enhance comfort along the lower regions of the face, i.e., jaws when talking, chin, lips, by expanding when a user speaks or when a larger head dons the mask 100. In one embodiment, the plurality of lower pleats 120*a-c* extend between the pair of lower lateral edges 116*a-b*.

In other embodiments, a plurality of lower cords 140*a-d* attach from a predetermined distance away from the lower face lateral edges 116*a-b* of the lower face panel 112. The lower cords 140*a-d* may include four equidistant cords, bands, strings, and such that can be tied behind the head as the lower face panel 112 is oriented over the lower regions of the face. The free ends 134 of the lower cords 140*a-d* can be tied together to secure the mask 100 to the forehead. The cords 140*a-d* do not necessarily have to be tied around the lower face for the mask 100 to remain attached to the head or face. The plurality of upper cords 140*a-d* may include, without limitation, string fasteners, rubber bands, and elastic ropes.

The plurality of lower cords 140*a-d* are defined by a lower mount end 142 and a lower free end 144. The lower mount end 142 is disposed to fixedly attach at a lower predetermined distance 136 from the pair of lower lateral edges 116*a*, 116*b*. By not attaching the lower cords 140*a-d* at the lower lateral edges 116*a-b*, but rather a distance inside the lateral edges 116*-ab*, a space is created that forms a lower flap 138 at the lower face lateral edges 116*-ab* of the lower face. In one embodiment, the lower predetermined distance 136 between the lower mount end 142 of the lower cords 140*a-d* and the lower lateral edges 116*a-b* is approximately between ¼" to 2". This space is what creates a flap, and thereby a space for airflow around the mouth. The flap 138 folds inwardly, away from the lower face outer surface 118.

In some embodiments, the mask 100 further comprises a mid-face panel 122 that is defined by a pair of mid-face longitudinal edges 124*a*, 124*b*, a pair of mid-face lateral edges 126*a*, 126*b*, a mid-face inner surface, and a mid-face outer surface 128. The mid-face panel 122 is disposed between, and generally coplanar to the forehead and lower face panels 102,112. The mid-face panel 122 is sized and dimensioned to generally cover the eyes and middle area of the face.

The mid-face panel 122 is unique in that its transparent characteristic allows for visibility. For example, the user can see through the mid-face panel 122 while being spray tanned. The mid-face panel 122 is generally elongated, resilient, and at least partially transparent. However, unlike the forehead panel 102 and the lower face panel 112, the mid-face panel 122 is not pleated, since pleats may compromise a clear vision. Suitable materials for the mid-face panel 122 may include, without limitation, a soft polyvinyl chloride, a Poly(methyl methacrylate), a polyethylene, and a silicone.

FIG. 3 illustrates a flowchart diagram of an exemplary method 200 for donning the pleated spray tan mask 100. The method 200 may include an initial Step 202 of engaging the forehead with a forehead panel 102. The method 200 may further comprise a Step 204 of engaging the eyes with a mid-face panel 122, the mid-face panel 122 being at least partially transparent. A Step 206 includes engaging the mouth with a lower face panel 112.

In some embodiments, a Step 208 comprises tying a plurality of upper cords 130*a*, 130*b* from the forehead panel 102 around the head. A Step 210 includes forming an upper flap at an upper lateral edge of the forehead panel 102. In some embodiments, a Step 212 may include tying a plurality of lower cords 140*a-d* from the lower face panel 112 around the head. A Step 214 comprises forming a lower flap 138 at a lower lateral edge of the lower face panel 112. A Step 216 may include breathing through flaps. In one embodiment, a Step 218 comprises expanding the mask 100 with the plurality of upper pleats 110*a-b* that form in the forehead panel 102. A final Step 220 includes expanding the mask 100 with the plurality of lower pleats 120*a-c* that form in the lower face panel 112.

It is also significant to note that prior to donning the mask, the spray tanning procedure may require at least some of the following preparatory steps for the rest of the body that is not covered by the mask 100. For example, initially, a user preferably shaves or waxes the skin before commencing the spray tanning. Often, this can be performed a day or two before so that the pores close. But that only applies if the solution is dark or has a bronzer in it. If it's a clear solution, it is possible to shave or wax the day of.

A second step may include exfoliating the body skin the day before the spray tanning appointment. Based on the way self-tanners work, it's important to slough off as much dead and dry skin as possible before applying the tanning composition. Another preferable step is to remove moisturizers, makeup and deodorant before applying the tanning composition. These products contain ingredients like oils that can make it hard for the main ingredient in the tanning composition to bind to the skin. This could cause the tanning composition to look streaky and blotchy.

It may also be beneficial to apply a Vaseline or lubricant immediately prior to application of the tanning composition. This can be applied to the knees, ankles, elbows, and palms. The lubricant protects such areas from absorbing too much DHA. At this point, the skin is ready for the spray tanning, and the mask can be donned, as described above in the method 200. Finally, it is advisable to maintain the tanning composition on overnight and not to put on any moisturizer until the next day. This includes no showering, using soap, or any moisturizer for at least 8 hours.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A mask for covering a face, the mask comprising:
   a forehead panel defined by a pair of forehead longitudinal edges, a pair of forehead lateral edges, and a forehead outer surface, the forehead panel being generally elongated, flat, and resilient;

a plurality of upper pleats forming on the forehead outer surface, the plurality of upper pleats extending along the length of the forehead panel, the plurality of upper pleats configured to enable expansion of the forehead panel to stretch across and substantially cover the forehead of the face;

a lower face panel defined by a pair of lower face longitudinal edges, a pair of lower face lateral edges, and a lower face outer surface, the lower face panel being generally elongated, flat, and resilient;

a plurality of lower pleats forming on the lower face outer surface, the plurality of lower pleats extending along the length of the lower face panel, the plurality of lower pleats configured to enable expansion of the lower face panel to cover the mouth and cheek areas of the face;

a mid-face panel defined by a pair of mid-face longitudinal edges, a pair of mid-face lateral edges, a mid-face inner surface, and a mid-face outer surface, the mid-face panel being at least partially transparent, the mid-face panel further being generally elongated, flat, and resilient;

a plurality of upper cords configured to enable fastening of the forehead panel and the mid-face panel, the plurality of upper cords defined by an upper mount end and an upper free end, the upper mount end disposed to fixedly attach to the pair of forehead lateral edges; and a plurality of lower cords configured to enable fastening of the lower face panel and the mid-face panel, the plurality of lower cords defined by a lower mount end and a lower free end, the lower mount end disposed to fixedly attach at a lower predetermined distance from the pair of lower face lateral edges, whereby a lower flap forms in the region of the lower predetermined distance.

2. The mask of claim 1, wherein the plurality of upper pleats extend between the pair of forehead lateral edges.

3. The mask of claim 1, wherein the plurality of lower pleats extend between the pair of lower face lateral edges.

4. The mask of claim 1, wherein the mid-face panel includes at least one of the following: a soft polyvinyl chloride, a Poly(methyl methacrylate), a polyethylene, and a silicone.

5. The mask of claim 1, wherein the plurality of upper cords include at least one of the following: two string fasteners, two rubber bands, and two elastic ropes.

6. The mask of claim 1, wherein the plurality of lower cords include at least one of the following: four string fasteners, four rubber bands, and four elastic ropes.

7. The mask of claim 1, wherein the upper and lower cords comprises a polyester, a cotton, or combinations thereof.

8. The mask of claim 1, wherein the lower predetermined distance between the lower mount end of the plurality of lower cords and the pair of lower face lateral edges is approximately between ¼ inch to 2 inches.

9. The mask of claim 1, wherein the pair of forehead longitudinal edges and the pair of forehead lateral edges are reinforced.

10. The mask of claim 1, wherein the pair of lower face longitudinal edges and the pair of lower face lateral edges are reinforced.

11. The mask of claim 1, wherein the lower flap folds inwardly, away from the lower face outer surface.

12. The mask of claim 1, wherein the forehead panel and the lower face panel comprise a filtering material.

13. The mask of claim 12, wherein the filtering material comprises a particulate filter.

14. A mask for covering a face, the mask consisting of:

a forehead panel defined by a pair of forehead longitudinal edges, a pair of forehead lateral edges, and a forehead outer surface, the forehead panel being generally elongated, flat, and resilient;

a plurality of upper pleats forming on the forehead outer surface, the plurality of upper pleats extending between the pair of forehead lateral edges, the plurality of upper pleats configured to enable expansion of the forehead panel to stretch across and substantially cover the forehead of the face;

a lower face panel defined by a pair of lower face longitudinal edges, a pair of lower face lateral edges, and a lower face outer surface, the lower face panel being generally elongated, flat, and resilient;

a plurality of lower pleats forming on the lower face outer surface, the plurality of lower pleats extending between the pair of lower face lateral edges, the plurality of lower pleats configured to enable expansion of the lower face panel to cover the mouth and cheek areas of the face;

a mid-face panel defined by a pair of mid-face longitudinal edges, a pair of mid-face lateral edges, a mid-face inner surface, and a mid-face outer surface, the mid-face panel being at least partially transparent, the mid-face panel further being generally elongated, flat, and resilient;

a plurality of upper cords configured to enable fastening of the forehead panel and the mid-face panel, the plurality of upper cords defined by an upper mount end and an upper free end, the upper mount end disposed to fixedly attach to the pair of forehead lateral edges; and a plurality of lower cords configured to enable fastening of the lower face panel and the mid-face panel, the plurality of lower cords defined by a lower mount end and a lower free end, the lower mount end disposed to fixedly attach at a lower predetermined distance from the pair of lower face lateral edges, the lower predetermined distance being approximately between 1;4 inch to 2 inches, whereby a lower flap forms in the region of the lower predetermined distance, the lower flap being configured to fold inwardly, away from the lower face outer surface.

15. The mask of claim 14, wherein the pair of forehead longitudinal edges and the pair of forehead lateral edges are reinforced.

16. The mask of claim 14, wherein the pair of lower face longitudinal edges and the pair of lower face lateral edges are reinforced.

17. The mask of claim 14, wherein the forehead panel comprises a filtering material.

18. The mask of claim 17, wherein the lower face panel comprises the filtering material.

19. A method for mask for covering a face, the method comprising:

engaging the forehead with a forehead panel, the forehead panel forming a plurality of upper pleats to be stretched across and substantially cover the forehead of the face;

engaging the eyes with a mid-face panel, the mid-face panel being at least partially transparent;

engaging the mouth with a lower face panel, the lower face panel forming a plurality of lower pleats to be stretched across the mouth and cheek areas of the face;

tying a plurality of upper cords from the forehead panel around the head; forming an upper flap at an upper lateral edge of the forehead panel;

tying a plurality of lower cords from the lower face panel around the head; forming a lower flap at a lower lateral edge of the lower face panel; breathing through the flaps;

expanding the mask with the plurality of upper pleats that form in the forehead panel; and expanding the mask with the plurality of lower pleats that form in the lower face panel.

\* \* \* \* \*